US008076258B1

(12) United States Patent
Biberger (10) Patent No.: US 8,076,258 B1
(45) Date of Patent: Dec. 13, 2011

(54) METHOD AND APPARATUS FOR MAKING RECYCLABLE CATALYSTS

(75) Inventor: Maximilian A. Biberger, Scottsdale, AZ (US)

(73) Assignee: SDCmaterials, Inc., Tempe, AZ (US)

( * ) Notice: Subject to any disclaimer, the term of this patent is extended or adjusted under 35 U.S.C. 154(b) by 285 days.

(21) Appl. No.: 12/152,098

(22) Filed: May 9, 2008

Related U.S. Application Data

(60) Provisional application No. 60/928,946, filed on May 11, 2007.

(51) Int. Cl.
*B01J 31/00* (2006.01)
*C01B 31/08* (2006.01)

(52) U.S. Cl. ........................ 502/104; 502/421
(58) Field of Classification Search .................. None
See application file for complete search history.

(56) References Cited

U.S. PATENT DOCUMENTS

| | | | | |
|---|---|---|---|---|
| 2,419,042 | A | 4/1947 | Todd | 202/205 |
| 2,519,531 | A | 8/1950 | Worn | 230/95 |
| 2,562,753 | A | 7/1951 | Trost | |
| 2,689,780 | A | 9/1954 | Rice | 23/106 |
| 3,001,402 | A | 9/1961 | Koblin | 73/421.5 |
| 3,067,025 | A | 12/1962 | Chisholm | |
| 3,178,121 | A | 4/1965 | Wallace, Jr. | |
| 3,401,465 | A | 9/1968 | Larwill | |
| 3,457,788 | A | 7/1969 | Miyajima | 73/422 |
| 3,537,513 | A | 11/1970 | Austin et al. | 165/70 |
| 3,741,001 | A | 6/1973 | Fletcher et al. | 73/28 |
| 3,752,172 | A | 8/1973 | Cohen et al. | |
| 3,774,442 | A | 11/1973 | Gustavsson | 73/28 |
| 3,830,756 | A | 8/1974 | Sanchez et al. | |
| 3,892,882 | A | 7/1975 | Guest et al. | |
| 3,914,573 | A | 10/1975 | Muehlberger | |
| 3,959,420 | A | 5/1976 | Geddes et al. | 261/112 |
| 4,008,620 | A | 2/1977 | Narato et al. | 73/421.5 A |

(Continued)

FOREIGN PATENT DOCUMENTS

JP 56-146804 11/1981

(Continued)

OTHER PUBLICATIONS

J. Heberlein, "New Approaches in Thermal Plasma Technology", Pure Appl. Chem., vol. 74, No. 3, 2002, pp. 327-335.

(Continued)

*Primary Examiner* — Melvin Mayes
*Assistant Examiner* — Sheng H Davis
(74) *Attorney, Agent, or Firm* — Haverstock & Owens LLP (57) ABSTRACT

A method of producing a fixed-bed catalyst with nano-scale structure using a nano-powder production reactor and a filter, the method comprising: introducing a starting powder into the reactor, wherein the starting powder comprises catalyst material; the reactor nano-sizing the starting powder, thereby producing an output, wherein the output comprises a nano-powder entrained in a fluid stream, the nano-powder comprising a plurality of nano-particles, each nano-particle comprising the catalyst material; introducing the output from the reactor to the filter structure, wherein the filter structure is fluidly coupled to the reactor; the filter structure separating the nano-particles from the fluid stream, wherein the fluid stream flows through the filter structure, while the filter structure collects the nano-particles, thereby forming a structured collection of catalytic nano-particles on the filter structure; and removing the filter structure from the reactor, wherein the structured collection of catalytic nano-particles is maintained for use as a fixed-bed catalyst.

22 Claims, 4 Drawing Sheets

U.S. PATENT DOCUMENTS

| | | | | |
|---|---|---|---|---|
| 4,018,388 | A | | 4/1977 | Andrews |
| 4,139,497 | A | * | 2/1979 | Castor et al. .................. 502/312 |
| 4,157,316 | A | | 6/1979 | Thompson et al. |
| 4,171,288 | A | | 10/1979 | Keith et al. |
| 4,174,298 | A | | 11/1979 | Antos |
| 4,248,387 | A | | 2/1981 | Andrews |
| 4,284,609 | A | | 8/1981 | deVries |
| 4,388,274 | A | * | 6/1983 | Rourke et al. ................. 422/177 |
| 4,431,750 | A | | 2/1984 | McGinnis et al. |
| 4,436,075 | A | | 3/1984 | Campbell et al. ............. 123/557 |
| 4,513,149 | A | | 4/1985 | Gray et al. |
| 4,764,283 | A | | 8/1988 | Ashbrook et al. |
| 4,824,624 | A | | 4/1989 | Palicka et al. ................... 264/67 |
| 4,855,505 | A | | 8/1989 | Koll |
| 4,866,240 | A | | 9/1989 | Webber |
| 4,983,555 | A | | 1/1991 | Roy et al. ...................... 501/120 |
| 4,987,033 | A | | 1/1991 | Abkowitz et al. ............. 428/469 |
| 5,041,713 | A | | 8/1991 | Weidman |
| 5,043,548 | A | | 8/1991 | Whitney et al. .......... 219/121.84 |
| 5,070,064 | A | | 12/1991 | Hsu et al. |
| 5,073,193 | A | | 12/1991 | Chaklader et al. ............... 75/346 |
| 5,157,007 | A | | 10/1992 | Domesle et al. |
| 5,369,241 | A | | 11/1994 | Taylor et al. ............. 219/121.47 |
| 5,371,049 | A | | 12/1994 | Moffett et al. .................. 501/89 |
| 5,372,629 | A | | 12/1994 | Anderson et al. ............... 75/332 |
| 5,392,797 | A | | 2/1995 | Welch ............................ 134/108 |
| 5,439,865 | A | | 8/1995 | Abe et al. |
| 5,442,153 | A | | 8/1995 | Marantz et al. |
| 5,485,941 | A | | 1/1996 | Guyomard et al. ................ 222/1 |
| 5,534,149 | A | * | 7/1996 | Birkenbeil et al. ............ 210/636 |
| 5,553,507 | A | | 9/1996 | Basch et al. .................. 73/863.01 |
| 5,611,896 | A | | 3/1997 | Swanepoel et al. ............ 204/169 |
| 5,630,322 | A | | 5/1997 | Heilmann et al. ................. 62/95 |
| 5,749,938 | A | | 5/1998 | Coombs .......................... 75/332 |
| 5,776,359 | A | | 7/1998 | Schultz et al. .............. 252/62.51 |
| 5,788,738 | A | | 8/1998 | Pirzada et al. ................... 75/331 |
| 5,811,187 | A | | 9/1998 | Anderson et al. ............. 428/403 |
| 5,837,959 | A | | 11/1998 | Muehlberger et al. |
| 5,851,507 | A | | 12/1998 | Pirzada et al. |
| 5,853,815 | A | | 12/1998 | Muehlberger ................ 427/446 |
| 5,905,000 | A | | 5/1999 | Yadav et al. ..................... 429/33 |
| 5,935,293 | A | | 8/1999 | Detering et al. ............. 75/10.19 |
| 5,989,648 | A | | 11/1999 | Phillips ......................... 427/456 |
| 5,993,967 | A | | 11/1999 | Brotzman, Jr. et al. ........ 428/407 |
| 5,993,988 | A | | 11/1999 | Ohara et al. ...................... 429/40 |
| 6,012,647 | A | | 1/2000 | Ruta et al. ................... 239/132.1 |
| 6,033,781 | A | | 3/2000 | Brotzman, Jr. et al. ........ 428/405 |
| 6,059,853 | A | | 5/2000 | Coombs .......................... 75/332 |
| 6,102,106 | A | | 8/2000 | Manning et al. ................ 165/76 |
| 6,213,049 | B1 | | 4/2001 | Yang |
| 6,214,195 | B1 | | 4/2001 | Yadav et al. ................... 205/334 |
| 6,228,904 | B1 | | 5/2001 | Yadav et al. ................... 523/210 |
| 6,254,940 | B1 | | 7/2001 | Pratsinis et al. ............... 427/562 |
| 6,261,484 | B1 | | 7/2001 | Phillips et al. ..................... 264/5 |
| 6,267,864 | B1 | | 7/2001 | Yadav et al. ................... 205/341 |
| 6,342,465 | B1 | | 1/2002 | Klein et al. |
| 6,344,271 | B1 | | 2/2002 | Yadav et al. ................... 428/402 |
| 6,379,419 | B1 | | 4/2002 | Celik et al. ....................... 75/346 |
| 6,387,560 | B1 | | 5/2002 | Yadav et al. ..................... 429/45 |
| 6,395,214 | B1 | | 5/2002 | Kear et al. ..................... 264/434 |
| 6,398,843 | B1 | | 6/2002 | Tarrant ............................ 75/249 |
| 6,409,851 | B1 | | 6/2002 | Sethuram et al. ............. 148/565 |
| 6,413,781 | B1 | | 7/2002 | Geis et al. |
| 6,416,818 | B1 | | 7/2002 | Aikens et al. ............... 427/383.1 |
| RE37,853 | E | | 9/2002 | Detering et al. ............. 75/10.19 |
| 6,444,009 | B1 | | 9/2002 | Liu et al. ......................... 75/332 |
| 6,517,800 | B1 | | 2/2003 | Cheng et al. ................ 423/447.1 |
| 6,524,662 | B2 | | 2/2003 | Jang et al. ..................... 427/535 |
| 6,531,704 | B2 | | 3/2003 | Yadav et al. ................. 250/493.1 |
| 6,548,445 | B1 | | 4/2003 | Buysch et al. |
| 6,554,609 | B2 | | 4/2003 | Yadav et al. ...................... 432/9 |
| 6,562,495 | B2 | | 5/2003 | Yadav et al. ..................... 429/12 |
| 6,569,397 | B1 | | 5/2003 | Yadav et al. ................... 423/345 |
| 6,569,518 | B2 | | 5/2003 | Yadav et al. ................... 428/323 |
| 6,572,672 | B2 | | 6/2003 | Yadav et al. ................... 75/343 |
| 6,596,187 | B2 | | 7/2003 | Coll et al. |
| 6,603,038 | B1 | | 8/2003 | Hagemeyer et al. |
| 6,607,821 | B2 | | 8/2003 | Yadav et al. ................... 428/323 |
| 6,610,355 | B2 | | 8/2003 | Yadav et al. ................... 427/115 |
| 6,623,559 | B2 | | 9/2003 | Huang |
| 6,635,357 | B2 | | 10/2003 | Moxson et al. ................ 428/548 |
| 6,641,775 | B2 | | 11/2003 | Vigliotti et al. ................ 264/618 |
| 6,652,822 | B2 | | 11/2003 | Phillips et al. ................. 423/290 |
| 6,652,967 | B2 | | 11/2003 | Yadav et al. ................... 428/403 |
| 6,669,823 | B1 | | 12/2003 | Sarkas et al. .................. 204/164 |
| 6,682,002 | B2 | | 1/2004 | Kyotani ......................... 239/318 |
| 6,689,192 | B1 | | 2/2004 | Phillips et al. .................. 75/342 |
| 6,699,398 | B1 | | 3/2004 | Kim ................................ 216/55 |
| 6,706,097 | B2 | | 3/2004 | Zornes ............................ 96/153 |
| 6,710,207 | B2 | | 3/2004 | Bogan, Jr. et al. |
| 6,713,176 | B2 | | 3/2004 | Yadav et al. ................... 428/402 |
| 6,716,525 | B1 | | 4/2004 | Yadav et al. ................... 428/402 |
| 6,746,791 | B2 | | 6/2004 | Yadav et al. ..................... 429/30 |
| 6,772,584 | B2 | | 8/2004 | Chun et al. ....................... 60/275 |
| 6,786,950 | B2 | | 9/2004 | Yadav et al. ..................... 75/346 |
| 6,813,931 | B2 | | 11/2004 | Yadav et al. ................... 73/31.05 |
| 6,817,388 | B2 | | 11/2004 | Tsangaris et al. .............. 141/82 |
| 6,832,735 | B2 | | 12/2004 | Yadav et al. ..................... 241/16 |
| 6,838,072 | B1 | | 1/2005 | Kong et al. ................... 423/594.2 |
| 6,855,426 | B2 | | 2/2005 | Yadav ............................ 428/403 |
| 6,855,749 | B1 | | 2/2005 | Yadav et al. ................... 523/105 |
| 6,886,545 | B1 | | 5/2005 | Holm ......................... 123/568.21 |
| 6,896,958 | B1 | | 5/2005 | Cayton et al. ................. 428/323 |
| 6,902,699 | B2 | | 6/2005 | Fritzemeier et al. ............ 419/38 |
| 6,916,872 | B2 | | 7/2005 | Yadav et al. ................... 524/430 |
| 6,919,527 | B2 | | 7/2005 | Boulos et al. ............. 219/121.52 |
| 6,933,331 | B2 | | 8/2005 | Yadav et al. ................... 523/210 |
| 6,986,877 | B2 | | 1/2006 | Takikawa et al. .......... 423/447.3 |
| 6,994,837 | B2 | | 2/2006 | Boulos et al. ................. 423/613 |
| 7,007,872 | B2 | | 3/2006 | Yadav et al. ...................... 241/1 |
| 7,052,777 | B2 | | 5/2006 | Brotzman, Jr. et al. ....... 428/570 |
| 7,073,559 | B2 | | 7/2006 | O'Larey et al. .............. 164/76.1 |
| 7,081,267 | B2 | | 7/2006 | Yadav ........................... 427/115 |
| 7,101,819 | B2 | | 9/2006 | Rosenflanz et al. ............ 501/10 |
| 7,147,544 | B2 | | 12/2006 | Rosenflanz .................... 451/28 |
| 7,147,894 | B2 | | 12/2006 | Zhou et al. .................... 427/256 |
| 7,166,198 | B2 | | 1/2007 | Van Der Walt et al. ....... 204/165 |
| 7,166,663 | B2 | | 1/2007 | Cayton et al. ................. 524/430 |
| 7,172,649 | B2 | | 2/2007 | Conrad et al. .................. 106/35 |
| 7,178,747 | B2 | | 2/2007 | Yadav et al. ..................... 241/23 |
| 7,208,126 | B2 | | 4/2007 | Musick et al. ................... 423/69 |
| 7,211,236 | B2 | | 5/2007 | Stark et al. ................. 423/592.1 |
| 7,217,407 | B2 | | 5/2007 | Zhang ............................ 423/610 |
| 7,307,195 | B2 | | 12/2007 | Polverejan et al. ............ 585/443 |
| 7,323,655 | B2 | | 1/2008 | Kim ........................ 219/121.43 |
| 7,384,447 | B2 | | 6/2008 | Kodas et al. .................... 75/332 |
| 7,417,008 | B2 | | 8/2008 | Richards et al. |
| 7,494,527 | B2 | | 2/2009 | Jurewicz et al. |
| 7,541,012 | B2 | | 6/2009 | Yeung et al. |
| 7,572,315 | B2 | | 8/2009 | Boulos et al. |
| 7,611,686 | B2 | | 11/2009 | Alekseeva et al. |
| 7,615,097 | B2 | | 11/2009 | McKechnie et al. |
| 7,622,693 | B2 | | 11/2009 | Foret |
| 7,803,210 | B2 | * | 9/2010 | Sekine et al. ................... 75/334 |
| 2001/0042802 | A1 | | 11/2001 | Youds |
| 2002/0068026 | A1 | * | 6/2002 | Murrell et al. ................. 422/211 |
| 2002/0079620 | A1 | | 6/2002 | DuBuis et al. ............ 264/328.14 |
| 2002/0143417 | A1 | | 10/2002 | Ito et al. |
| 2002/0182735 | A1 | | 12/2002 | Kibby et al. |
| 2003/0036786 | A1 | | 2/2003 | Duren et al. .................... 607/96 |
| 2003/0042232 | A1 | | 3/2003 | Shimazu |
| 2003/0066800 | A1 | | 4/2003 | Saim et al. |
| 2003/0108459 | A1 | | 6/2003 | Wu et al. .................. 422/186.04 |
| 2003/0139288 | A1 | | 7/2003 | Cai et al. |
| 2003/0172772 | A1 | | 9/2003 | Sethuram et al. |
| 2003/0223546 | A1 | | 12/2003 | McGregor et al. ............ 378/143 |
| 2004/0009118 | A1 | | 1/2004 | Phillips et al. |
| 2004/0023302 | A1 | | 2/2004 | Archibald et al. |
| 2004/0023453 | A1 | | 2/2004 | Xu et al. |
| 2004/0103751 | A1 | | 6/2004 | Joseph et al. ................. 75/10.19 |
| 2004/0127586 | A1 | | 7/2004 | Jin et al. |
| 2004/0167009 | A1 | | 8/2004 | Kuntz et al. ................... 501/95.2 |
| 2004/0176246 | A1 | * | 9/2004 | Shirk et al. .................... 502/439 |
| 2004/0213998 | A1 | | 10/2004 | Hearley et al. |
| 2004/0251017 | A1 | | 12/2004 | Pillion et al. .................. 165/289 |
| 2005/0000321 | A1 | | 1/2005 | O'Larey et al. ................ 75/952 |
| 2005/0000950 | A1 | | 1/2005 | Schroder et al. ......... 219/121.59 |

| | | | |
|---|---|---|---|
| 2005/0077034 A1 | 4/2005 | King | 165/163 |
| 2005/0097988 A1 | 5/2005 | Kodas et al. | 75/332 |
| 2005/0199739 A1 | 9/2005 | Kuroda et al. | |
| 2005/0220695 A1* | 10/2005 | Abatzoglou et al. | 423/445 R |
| 2005/0227864 A1* | 10/2005 | Sutorik et al. | 502/304 |
| 2005/0233380 A1 | 10/2005 | Pesiri et al. | 435/7.1 |
| 2005/0240069 A1 | 10/2005 | Polverejan et al. | 585/444 |
| 2005/0258766 A1 | 11/2005 | Kim | 315/111.21 |
| 2006/0051505 A1 | 3/2006 | Kortshagen et al. | 427/212 |
| 2006/0068989 A1* | 3/2006 | Ninomiya et al. | 502/339 |
| 2006/0094595 A1 | 5/2006 | Labarge | |
| 2006/0096393 A1 | 5/2006 | Pesiri | 73/863.21 |
| 2006/0105910 A1 | 5/2006 | Zhou et al. | |
| 2006/0108332 A1 | 5/2006 | Belashchenko | 219/121.47 |
| 2006/0153728 A1 | 7/2006 | Schoenung et al. | |
| 2006/0153765 A1 | 7/2006 | Pham-Huu et al. | |
| 2006/0159596 A1 | 7/2006 | De La Veaux et al. | 422/151 |
| 2006/0231525 A1 | 10/2006 | Asakawa et al. | 216/56 |
| 2007/0048206 A1 | 3/2007 | Hung et al. | |
| 2007/0063364 A1 | 3/2007 | Hsiao et al. | 264/5 |
| 2007/0084308 A1 | 4/2007 | Nakamura et al. | 75/346 |
| 2007/0084834 A1 | 4/2007 | Hanus et al. | 219/121.5 |
| 2007/0087934 A1 | 4/2007 | Martens et al. | 502/214 |
| 2007/0173403 A1 | 7/2007 | Koike et al. | |
| 2007/0253874 A1 | 11/2007 | Foret | |
| 2007/0292321 A1 | 12/2007 | Plischke et al. | |
| 2008/0031806 A1 | 2/2008 | Gavenonis et al. | |
| 2008/0064769 A1 | 3/2008 | Sato et al. | |
| 2008/0105083 A1 | 5/2008 | Nakamura et al. | |
| 2008/0116178 A1 | 5/2008 | Weidman | |
| 2008/0274344 A1 | 11/2008 | Vieth et al. | |
| 2008/0277267 A1 | 11/2008 | Biberger et al. | |
| 2009/0010801 A1 | 1/2009 | Murphy et al. | |
| 2009/0088585 A1 | 4/2009 | Schammel et al. | |
| 2009/0114568 A1 | 5/2009 | Trevino et al. | |
| 2009/0274903 A1 | 11/2009 | Addiego | |
| 2009/0286899 A1 | 11/2009 | Hofmann et al. | |

FOREIGN PATENT DOCUMENTS

| | | |
|---|---|---|
| SU | 493241 | 3/1976 |
| WO | WO 02/092503 A1 | 11/2002 |
| WO | 2004052778 A2 | 6/2004 |
| WO | WO 2006/079213 A1 | 8/2006 |

OTHER PUBLICATIONS

T. Yoshida, "The Future of Thermal Plasma Processing for Coating", Pure & Appl. Chem., vol. 66, No. 6, 1994 pp. 1223-1230.

A. Gutsch et al., "Gas-Phase Production of Nanoparticles", Kona No. 20, 2002, pp. 24-37.

Dr. Heike Mühlenweg et al., "Gas-Phase Reactions—Open Up New Roads to Nanoproducts", Degussa ScienceNewsletter No. 08, 2004, pp. 12-16.

Coating Generation: Vaporization of Particles in Plasma Spraying and Splat Formation, M. Vardelle, A. Vardelle, K-I li, P. Fauchais, Universite de Limoges, 123 Avenue A. Thomas 87000, Limoges, F. , Pure & Chem, vol. 68, No. 5, pp. 1093-1099, 1996.

United States Patent and Trademark Office, Notice of Allowance, mailed Oct. 27, 2009, U.S. Appl. No. 12/151,932, filed May 8, 2008, First Named Inventor: Rob Kevwitch.

H. Konrad et al., "Nanostructured Cu-Bi Alloys Prepared by Co-Evaporation in a Continuous Gas Flow," NanoStructured Materials, vol. 7, No. 6, Apr. 1996, pp. 605-610.

M.Vardelle et al., "Experimental Investigation of Powder Vaporization in Thermal Plasma Jets," Plasma Chemistry and Plasma Processing, vol. 11, No. 2, Jun. 1991, pp. 185-201.

P. Fauchais et al., "Plasma Spray: Study of the Coating Generation," Ceramics International, Elsevier, Amsterdam, NL, vol. 22, No. 4, Jan. 1996, pp. 295-303.

P. Fauchais et al., "Les Dépôts Par Plasma Thermique," Revue Generale De L'Electricitie, RGE. Paris, FR, No. 2, Jan. 1993, pp. 7-12.

P. Fauchais et al, "La Projection Par Plasma: Une Revue," Annales De Physique, vol. 14, No. 3, Jun. 1989, pp. 261-310.

Kenvin et al. "Supported Catalysts Prepared from Monouclear Copper Complexes: Catalytic Properties", Journal of Catalysis, pp. 81-91.

National Aeronautics and Space Administration, "Enthalpy", http://www.grc.nasa.gov/WWW/K-12/airplane/enthalpy.html, Nov. 23, 2009, 1 page.

Hanet al., Deformation Mechanisms and Ductility of Nanostructured Al Alloys, Mat. Res. Soc. Symp. Proc. vol. 821, Jan. 2004, Material Research Society, http://www.mrs.org/s_mrs/bin.asp?CID=2670&DOC=FILE.PDF., 6 pages.

United States Patent and Trademark Office, Office Action, mailed Feb. 19, 2010, U.S. Appl. No. 12/152,109, filed May 9, 2008, First Named Inventor: Maximilian A. Biberger, 17 pages.

Derwent English Abstract for Publication No. SU 193241 A, Application No. 1973SU1943286 filed on Jul. 2, 1973, published on Mar. 1, 1976, entitled Catalyst for Ammonia Synthesis Contains Oxides of Aluminium, Potassium, Calcium, Iron and Nickel Oxide for Increased Activity, 3 pgs.

Nagai, Yasutaka, et al., "Sintering Inhibition Mechanism of Platinum Supported on Ceria-based Oxide and Pt-oxide-support Interaction," Journal of Catalysis 242 (2006), pp. 103-109, Jul. 3, 2006, Elsevier.

* cited by examiner

METHOD AND APPARATUS FOR MAKING RECYCLABLE CATALYSTS

CROSS-REFERENCE TO RELATED APPLICATIONS

The present application claims priority to co-pending U.S. Provisional Application Ser. No. 60/928,946, filed May 11, 2007, entitled "MATERIAL PRODUCTION SYSTEM AND METHOD," which is hereby incorporated by reference as if set forth herein. The co-pending U.S. patent application Ser. No. 11/110,341, filed on Apr. 10, 2005, entitled, "HIGH THROUGHPUT DISCOVERY OF MATERIALS THROUGH VAPOR PHASE SYNTHESIS" is incorporated by reference.

FIELD OF THE INVENTION

The present invention relates to catalysts, primarily metal catalysts used in fixed bed catalysis of fluid flows, and to methods of reusing catalytic materials.

BACKGROUND OF THE INVENTION

Catalysts play many important roles in industry. One such role is fluid conditioning, including decontamination of flowing fluid. For example, a catalytic system might be employed to remove oxygen content from an inert gas flow. The "catalytic converter" employed in automobiles (circa. 2007 and earlier) removes certain pollutants from an exhaust flow produced by the engine. "Solid" catalysts—so-called because the catalytic compound exists in solid phase during use—are often employed in this role, as fluid decontamination typically involves removal of the contaminant from fluid phase, aerosol state, solution, or entrainment.

"Raney nickel", a solid phase catalyst formed of nickel grains bonded in a skeletal structure along with aluminum grains, performs many industrial roles, including fluid conditioning. A variety of similar catalysts employ other active materials, including iron or copper, instead of nickel, and other alloying components, such as zinc or silicon, instead of aluminum. Currently, all of these "Raney-style" catalysts are formed via processes essentially similar to the original recipe for Raney nickel.

A Raney-style process describes a multi-step method of forming a porous, active metal catalyst. First, a precursor is formed of at least a binary alloy of metals where one of the metals can be extracted. Second, the precursor is activated by extracting an alloy constituent leaving a porous residue comprising a metal that has catalytic activity. Such processes are described in, e.g. Raney, M. *Catalysts from Alloys*, Ind. Eng. Chem., 1940, 32, 1199; as well as U.S. Pat. Nos. 1,628,190; 1,915,473; 2,139,602; 2,461,396 and 2,977,327 to M. Raney. Commercial catalysts made by these type of processes are sold by W. R. Grace & Co. under the trademark RANEY® catalyst.

Often, additional materials are added and process parameters are varied to achieve a desired catalytic activity or function. Typically, the process parameters and additional materials included depend both on the active material employed and the catalytic function desired. Some added materials called "promoters" serve to enhance catalytic activity. A typical process parameter that is varied according to specific needs is the precursor alloy composition. For example, the precursor used for Raney nickel typically consists of equal amounts of nickel and aluminum by volume.

The traditional Raney-style process results in a collection of granular pieces, each with an internal porosity. Depending on their grain size, these particles are used in slurry or in packed-column systems as heterogeneous catalysts. Generally, larger particle sizes are required for use in packed-column systems. Traditionally, there is a tradeoff between surface area and particle size, with larger-sized particles having less surface area per unit volume. See, e.g. the background section of U.S. Pat. No. 4,895,994.

Although small powder catalysts have desirable surface area to volume characteristics, they are only suitable for batch processing and must be isolated after use. In order to avoid these disadvantages, a variety of processing regimes have been proposed to permit use of Raney particles in fixed-bed catalysis. For example, U.S. Pat. No. 4,895,994 describes a fixed bed catalyst shaped from Raney precursor mixed with a polymer, cured, and then activated via a leaching process. U.S. Pat. No. 5,536,694 describes a fixed-bed catalyst prepared from powders of Raney precursor mixed with a powder of its catalytically active component as a binder. However, these processes involve high sintering temperatures and thus cannot accommodate small, high surface-to-volume-ratio precursor particles (the sintering temperatures are sufficient to destroy the grain structure of the precursor alloy in small particles). Thus, lacking the high surface to volume ratio provided by the smallest precursor sizes, these approaches instead rely on macroporosity of the fixed bed structure to achieve high internal diffusion, making the most of their surface area.

Therefore, the smallest precursor particles suitable for fixed-bed catalyst production via traditional means are micron scale particles. For example, micron scale aluminum powder and micron scale nickel powder can be combined in a melt-based alloying step, thereby producing nickel-aluminum alloy in a variety of alloy phases. The nickel-aluminum alloy is then processed and activated, such as by a leaching apparatus, resulting in a bulk porous structure that is mostly nickel (although some aluminum may remain). Unfortunately, the smallest pores within the structure produced are micron scale. Additionally, traditional means can be very involved, requiring several procedural steps and a variety of different components, thereby consuming significant time and money.

What is needed in the art is a system and method for producing a catalyst having smaller particle size, and therefore larger surface area available for catalysis. What is also needed in the art is a system and method that enable the reuse of catalytic materials.

SUMMARY OF THE INVENTION

The embodiments of the present invention include methods of producing a catalyst with nano-scale structure, using the catalyst in fixed bed catalysis of fluid flows, and reusing the catalytic materials, and systems capable of performing these methods.

In one aspect of the present invention, a method of producing a fixed-bed catalyst with nano-scale structure using a nano-powder production reactor and a filter structure is disclosed. The method comprises introducing a starting powder comprising catalyst material into the nano-powder production reactor, and the nano-powder production reactor nano-sizing the starting powder, thereby producing an output. The output comprises a nano-powder entrained in a reactor fluid stream. The nano-powder comprises a plurality of nano-particles, with each nano-particle comprising the catalyst material. The output from the nano-powder production reactor may then be introduced to the filter structure, wherein the filter structure is fluidly coupled to the nano-powder production reactor. The filter structure separates the nano-particles from the reactor fluid stream, wherein the filter structure collects the nano-particles, thereby forming a structured collection of catalytic nano-particles on the filter structure. The filter structure can then be removed from the nano-powder production reactor, with the structured collection of catalytic nano-particles being maintained on the filter structure for use as a fixed-bed catalyst.

The step of nano-sizing the starting powder can include generating a plasma flow within the nano-powder production reactor, and applying the plasma flow to the starting powder.

The method can further comprise employing the structured collection of catalytic nano-particles on the filter structure as a fixed-bed catalyst for a catalysis fluid stream, thereby forming a structured collection of contaminated catalytic nano-particles on the filter structure and a product output. The catalysis fluid stream preferably comprises a desired material and an undesired material. The step of employing the structured collection as a fixed-bed catalyst comprises: flowing the catalysis fluid stream through the structured collection of contaminated catalytic nano-particles on the filter structure; and the structured collection of catalytic nano-particles on the filter structure catalyzing the removal of the undesired material from the catalysis fluid stream, wherein the structured collection is contaminated with the undesired material and product output comprises the desired material.

The method can further comprise harvesting the contaminated catalytic nano-particles from the filter structure, and processing the contaminated catalytic nano-particles to form recycled starting powder from the contaminated catalytic nano-particles, wherein the recycled starting powder comprises the catalyst material. The recycled starting powder can then be introduced into the nano-powder production reactor, and the nano-powder production reactor can nano-size the recycled starting powder, thereby producing an output. This output comprises a nano-powder entrained in a fluid stream, and the nano-powder comprising a plurality of nano-particles, with each nano-particle comprising the catalyst material.

In another aspect of the present invention, a system for making a fixed-bed catalyst with nano-scale structure is disclosed. The system comprises a nano-powder production reactor configured to receive a catalyst material and nano-size the catalyst material, thereby producing an output. The output comprises a nano-powder entrained in a reactor fluid stream, and the nano-powder comprises a plurality of nano-particles, with each nano-particle comprising the catalyst material. The system further comprises a filter structure fluidly coupled to the nano-powder production reactor and configured to receive the nano-powder and separate the nano-particles from the reactor fluid stream. The filter structure collects the nano-particles, thereby forming a structured collection of catalytic nano-particles on the filter structure.

The filter structure may be further configured to be de-coupled from the nano-powder production reactor, wherein the structured collection of catalytic nano-particles is maintained on the filter structure for use as a fixed-bed catalyst.

The system may also comprise an airlock structure configured to enable selective air-tight isolation of the structured collection of catalytic nano-particles for the de-coupling of the filter structure from the nano-powder production reactor; and enable selective exposure of the structured collection of catalytic nano-particles to a catalysis fluid stream after the de-coupling of the filter structure from the nano-powder production reactor. This airlock structure preferably comprises at least one valve disposed on the filter structure.

The system can further comprise a gas dispensing device fluidly coupled to the nano-powder production reactor and configured to provide a motive gas to the nano-powder production reactor, and a powder dispensing device fluidly coupled to the nano-powder production reactor and configured to provide the catalyst material in powder form to the nano-powder production reactor.

The system can further include an exhaust that is fluidly coupled downstream from the filter structure and configured to receive the filtered reactor fluid stream.

In the systems and methods of the present invention, the catalyst material is preferably a metal of the transition group VIII of the periodic table of elements. Examples of preferred metals include nickel, iron, and cobalt. In some embodiments, the catalyst material is copper. Preferably, the starting powder, recycled or not, is micron-scale, meaning it has an average grain size of at least 1 micron.

By forming the catalyst structure from nano-sized particles instead of micron-sized (or larger sized) particles, the present invention can significantly increase the total catalytic surface area, given that a nano-particle is significantly smaller than a micron particle thereby allowing for a greater quantity of nano-particles than micron particles. The nano-skeletal structure produced via the present invention preferably has a surface area of at least 10,000 times the surface area of a micron scale structure of the same volume. This increase in surface area results in massive cost savings.

Additionally, by using a filter structure to form a structured collection of catalytic nano-particles, the present invention can make the production and use of the catalytic structure significantly more efficient and can enable the reuse of catalytic materials.

DETAILED DESCRIPTION OF THE INVENTION

The description below concerns several embodiments of the present invention. The discussion references the illustrated preferred embodiment. However, the scope of the present invention is not limited to either the illustrated embodiment, nor is it limited to those discussed, to the contrary, the scope should be interpreted as broadly as possible based on the language of the Claims section of this document.

This disclosure refers to both particles and powders. These two terms are equivalent, except for the caveat that a singular "powder" refers to a collection of particles. The present invention may apply to a wide variety of powders and particles. Additionally, for the purposes of this disclosure, the terms nano-powders and nano-particles refer to powders and particles having an average grain size less than 250 nanometers and an aspect ratio between one and one million.

The present invention will be readily understood by the following detailed description in conjunction with the accompanying drawings. To facilitate this description, like reference numerals designate like elements.

The embodiments of the present invention revolve around the use of a nano-powder production reactor to produce nano-skeletal catalytic precursors. In general, vapor phase nano-powder production means are preferred. Most preferably, the embodiments of the present invention use nano-powder production systems similar to those disclosed in U.S. patent application Ser. No. 11/110,341, filed on Apr. 19, 2005 and entitled, "HIGH THROUGHPUT DISCOVERY OF MATERIALS THROUGH VAPOR PHASE SYNTHESIS", which is currently published as U.S. Publication No. 2005-0233380-A. In such a nano-powder production system, working gas is supplied from a gas source to a plasma reactor. Within the plasma reactor, energy is delivered to the working gas, thereby creating a plasma. A variety of different means can be employed to deliver this energy, including, but not limited to, DC coupling, capacitive coupling, inductive coupling, and resonant coupling. One or more material dispensing devices introduce at least one material, preferably in powder form, into the plasma reactor. The combination within the plasma reactor of the plasma and the material(s) introduced by the material dispensing device(s) forms a highly reactive and energetic mixture, wherein the powder can be vaporized. This mixture of vaporized powder moves through the plasma reactor in the flow direction of the working gas. As it moves, the mixture cools and particles are formed therein. The still-energetic output mixture, comprising hot gas and energetic particles, is emitted from the plasma reactor. Following emission from the plasma reactor, the output mixture cools further and is exposed to a sampling device, which selectively samples portions of the output mixture, which comprises hot gas and particles of relatively homogeneous size distribution. Each particle can comprise a combination of the materials introduced by the material dispensing devices. It is contemplated that other nano-powder production means, including non-vapor phase nano-powder production means, are within the scope of the present invention.

Figure 1A:
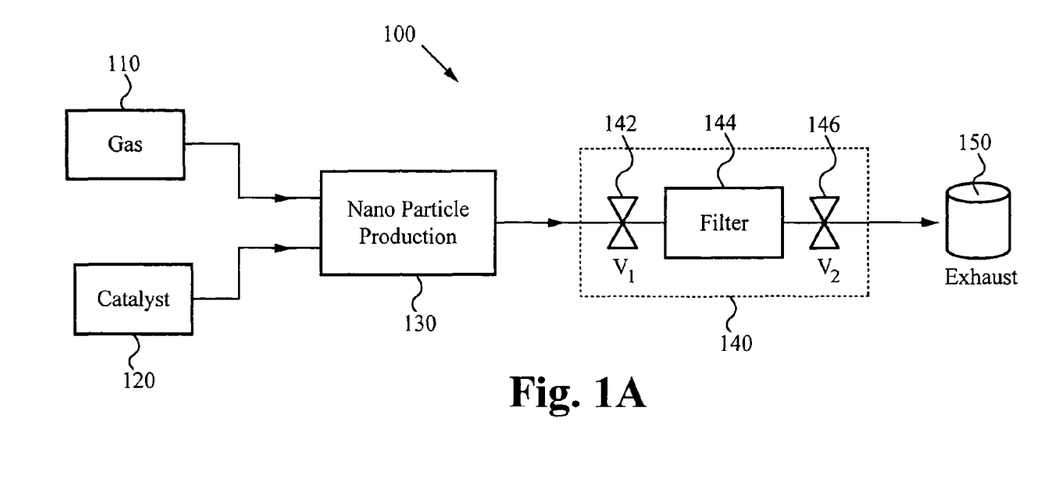
FIG. 1A is a schematic illustration of one embodiment of a system for producing a reusable filter-based catalyst in accordance with the principles of the present invention.

FIG. 1A illustrates one embodiment of a system 100 for producing a reusable filter-based catalyst with nano-scale structure. The system 100 comprises a nano-powder production reactor 130 and a filter structure 140 fluidly coupled to the nano-powder production reactor 130. The system 100 can further include a gas supply 110 and a catalyst material dispensing device 120, each fluidly coupled to the nano-powder production reactor 130. The gas supply 110 is configured to provide a motive gas to the reactor 130, while the dispensing device 120 is configured to provide a powder of a catalyst material into the nano-powder production reactor 130, thereby enabling the nano-powder production reactor 130 to produce an output comprising nano-powder catalyst material entrained in a fluid stream. Preferably, the fluid stream comprises a gas from the gas supply 110.

Figure 1B:
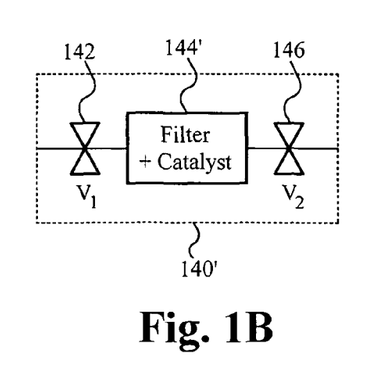
FIG. 1B is a schematic illustration of one embodiment of a reusable filter-based catalyst in accordance with the principles of the present invention.

The fluid stream from the reactor 130 flows to the filter structure 140. The filter structure 140 is configured to separate the nano-powder catalyst material from the fluid stream. The filter structure 140 collects the catalyst nano-particles, and in doing so, forms a structured collection of catalyst nano-particles, as will be discussed in further detail below with respect to FIG. 18.

In a preferred embodiment, the filter structure 140 comprises an air filter 144. However, it is contemplated that a variety of other means may be employed to separate the nano-powder from the fluid stream. The filter 144 is part of the filter structure 140. The filter structure 140 can also include a first valve 142 and a second valve 146. In a preferred embodiment, the first valve 142 and the second valve 146 are separately sealable and are substantially airtight when sealed. The first valve 142 is fluidly coupled to the output of the nano-powder production reactor 130 and serves as an input valve to the filter structure 140, while the second valve 146 is fluidly coupled to an exhaust 150 of the system and serves as an output valve of the filter structure 140. Upon receiving the fluid stream, the exhaust 150 can remove the received fluid stream and any remaining entrained material from the system 100. Additionally or alternatively, the exhaust 150 can recycle the received fluid stream and any remaining entrained material back into the system 100, such as by feeding it back into the nano-powder production reactor 130.

Figure 2A:
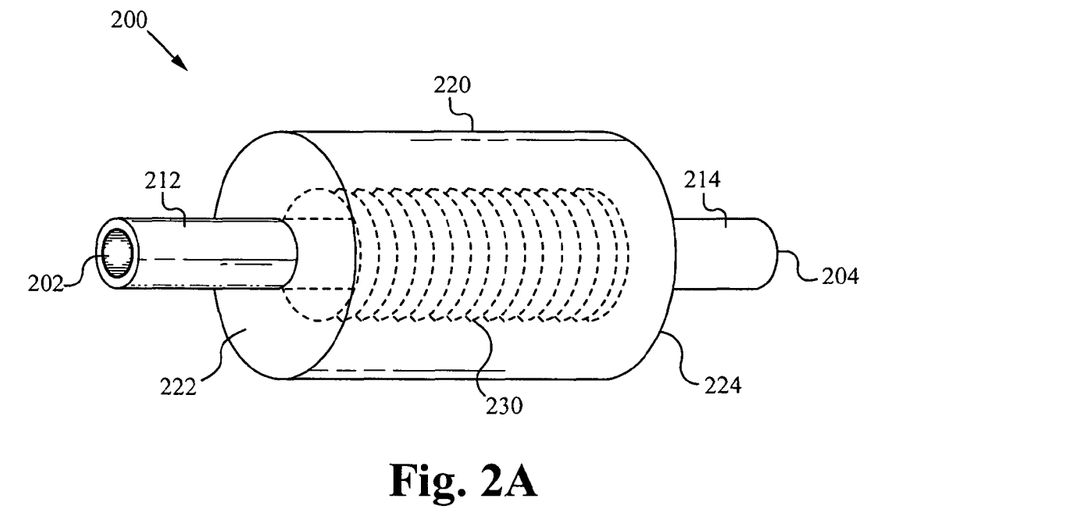
FIG. 2A is a partially transparent isometric view of one embodiment of a reusable filter structure in accordance with the principles of the present invention.

FIG. 2A illustrates an exemplary embodiment of a filter structure 200 in accordance with the principles of the present invention. The filter structure 200 preferably comprises a filter 230 housed within an output chamber 220. In a preferred embodiment, the filter structure 200 further comprises an inlet conduit 212 and an outlet conduit 214 each fluidly coupled to the filter 230. The inlet conduit 212 and the outlet conduit 214 form a conduit system that, along with the rest of the filter structure 200, is configured to receive a matter stream flowing into the inlet 202 of the inlet conduit 212, collect some, most or all of the particles from the stream, and deliver the remainder of the stream to the outlet 204 of the outlet conduit 214.

The outer structure of the filter structure 200 can include a cylindrical body, which forms the output chamber 220. This cylindrical body is preferably coupled to first and second axially directed end plates 222 and 224. In a preferred embodiment, the interfaces between the cylindrical body and the axially directed end plates 222 and 224 are sealed. In some embodiments, the cylindrical body and the end plates can be integrally formed.

Preferably, each axially directed end plate includes ports configurable to mate with a conduit structure. As shown, the first axially directed end plate 222 includes a main inlet coupled to the inlet conduit 212. Preferably, this coupling is sealed airtight and permits delivery of a matter stream from the inlet conduit 212 into the filter 230. Similarly, the second axially directed end plate 224 preferably includes a main outlet coupled to outlet conduit 214. This coupling can also be sealed airtight and can permit delivery, following particle collection, of a remainder of a matter stream to the outlet 204.

In one embodiment, the output chamber 220 has a longitudinal axis parallel with the axes of the inlet conduit 212 and the outlet conduit 214. The output chamber 220 can have a cylindrical shape and can form a radially directed surface, but narrow to meet the inlet conduit 212 and/or the outlet conduit 214. This narrowing can occur in the region of the first axially directed end plate 222 and or the second axially directed end plate 224. In some embodiments, the faces of the first and second axially directed end plates 222 and 224 are not completely axially directed, but instead form an angle with the axis of the chamber, so as to gradually narrow the output chamber 220. This configuration is preferred. In some embodiments, the inner surface of the output chamber 220 forms a curve as it narrows to meet the inlet conduit 212 and/or the outlet conduit 214.

The filter 230 and the output chamber 220 can be coupled with one another in a fixed position. This coupling can produce a narrowed channel, shaped like a cylindrical shell, between a radially directed outer surface of the filter 230 and the radially directed inner surface of the output chamber 220.

Figure 2B:
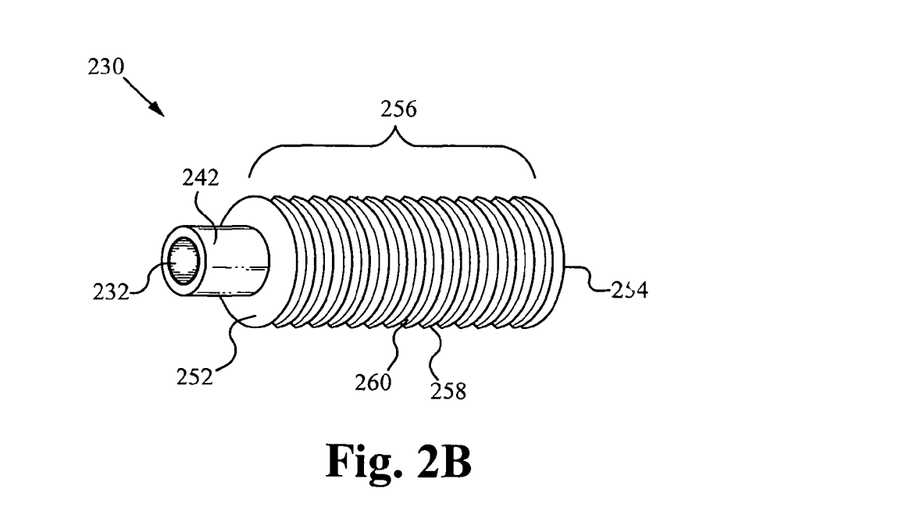
FIG. 2B is an isometric view of one embodiment of a reusable filter for producing reusable filter-based catalysts in accordance with the principles of the present invention.

FIG. 2B is an isometric view of the filter 230. In a preferred embodiment, a high efficiency particulate air (HEPA) filter is used. The filter 230 preferably includes structures for decelerating a matter stream, distributing the particle load evenly, and facilitating particle collection. The filter 230 preferably has an axis parallel with that of the output chamber 220, a first end 252 and a second end 254 opposite the first end 252. In a preferred embodiment, the filter 230 comprises an inlet conduit 242 at the first end 252 and an outlet conduit at the second end 254, each fluidly coupled to the interior of the filter 230. An inlet 232 of the inlet conduit 242 is fluidly coupled to the inlet conduit 212. The filter 230 preferably widens from the inlet 232 at its first end 252, with its walls forming a radially directed surface 256.

The filter 230 can comprise a set of filters and filter components, such as those represented by circumferential ridges 258 and 260. In some embodiments, the filters are radially directed and the ridges 258 and 260 represent surface-area-increasing features of the filters. In these embodiments, the second end 254 of the filter 230 is preferably a curved, non-porous surface that directs matter flow into the radially directed filters. In some embodiments the filters are axially directed and the ridges 258 and 260 represent edges of individual filters. In these embodiments, the second end 254 of the filter 230 is preferably a filter itself. Additionally, the filters can be arranged in series.

In operation, the catalyst dispensing device 120 provides a powder of a catalyst material into the nano-powder production reactor 130. Similarly, the gas supply 110 provides gas to the nano-powder production reactor 130. Upon reception of the catalyst powder and the gas, the reactor 130 produces an output comprising nano-powder catalyst material entrained in a fluid stream.

The output is provided to the filter structure 140, which separates the nano-powder catalyst material from the fluid stream. The remainder of the fluid stream flows to the exhaust 150, where it can be recycled for reuse, either with the gas supply 110 or via other means, and/or removed from the system 100. The catalyst nano-powder filtered by the filter structure 140 forms a structured collection of catalyst nano-particles, preferably within the filter structure 140.

When a sufficient amount of nano-powder is present in the structured collection, the filter structure 140 can be fluidly isolated from the nano-powder production reactor 130 and the exhaust 150. In a preferred embodiment, the first valve 142 and the second valve 146 are sealed to form airtight barriers, thereby preventing leakage from or contamination of the filter structure 140. Preferably, the second valve 146 is sealed prior to the sealing of the first valve 142, resulting in a slight pressurization of the filter structure 140.

Once sealed, the filter structure 140 can be removed from the system 100 of FIG. 1A. FIG. 1B illustrates the filter structure 140' containing the activated filter 144', which comprises the filter and the structured collection of catalyst nano-particles. The first valve 142 and the second valve 146 are sealed and the filter structure 140' is ready for integration into a system where it provides catalysis. By removing the filter structure from the system, the structured collection of catalytic nano-particles is removed and immediately available for use as a fixed-bed catalyst for fluid flows.

Preferably, airtight isolation and de-coupling of the filter structure from the nano-powder production reactor are facilitated by the use of valves, as discussed above. However, it is contemplated that a variety of airlock structures may be employed to permit selective airtight isolation and exposure of the structured collection of catalytic nano-particles.

In some embodiments, the system of the present invention further includes a dispensing device configured to provide a powder of a promoter material into the nano-powder production reactor 130, similar to dispensing device 120, thereby permitting the nano-powder production reactor 130 to produce an output comprising nano-powder promoter material entrained in a fluid stream. Such use of the promoter material may be employed with or without the use of catalyst material. In such embodiments, the filter structure 140 is preferably used to separate the nano powder promoter material from the fluid stream and to form a structured collection of promoter nano-particles, with or without catalyst material. The promoter material can include, but is not limited to, zinc, molybdenum, and chromium. In some embodiments, a single dispensing device is used for both promoter and catalyst materials.

In a preferred embodiment, the catalyst material is a metal of the transition group VIII of the periodic table of elements. Most preferably, the metal is selected from the group consisting of nickel, iron, and cobalt. In some embodiments, the catalyst material is copper.

Figure 3:
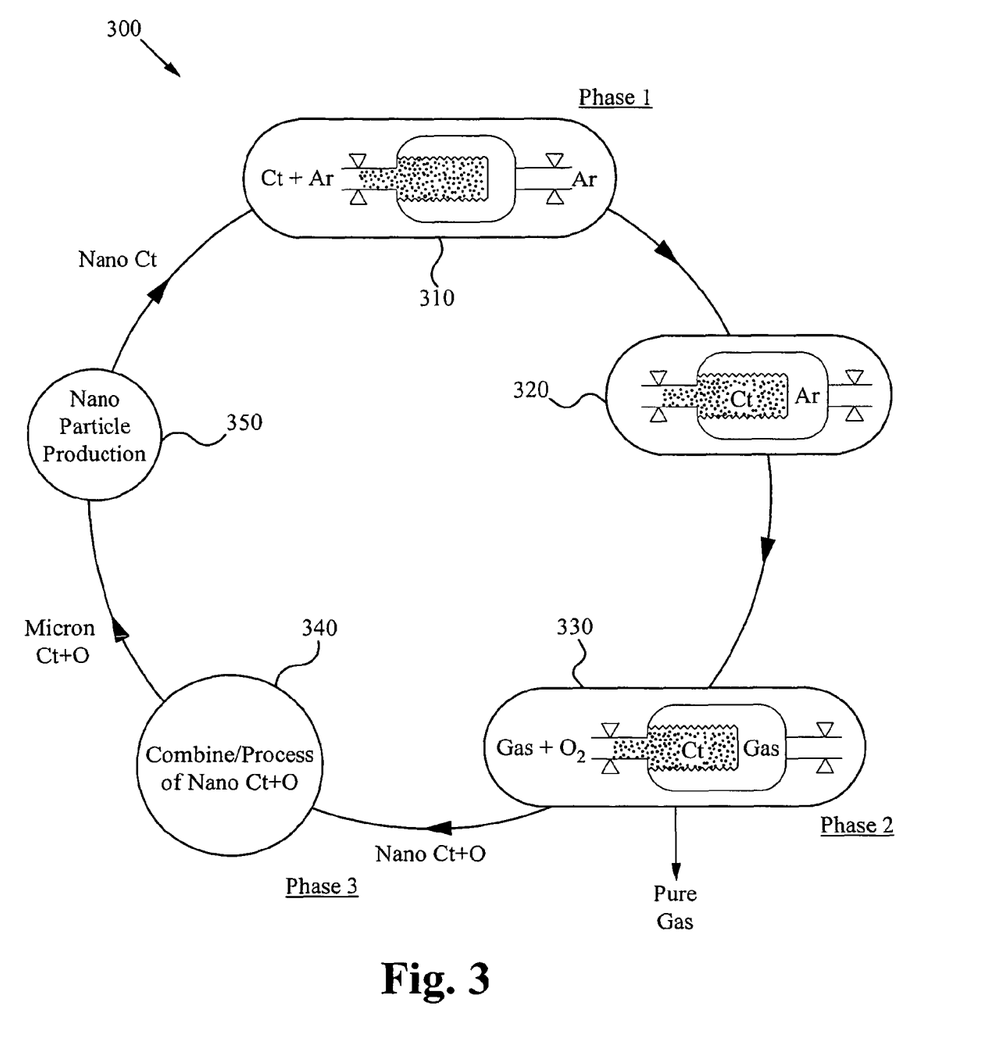
FIG. 3 is a schematic illustration of one embodiment of a life-cycle of a reusable filter-based catalyst in accordance with the principles of the present invention.

Some embodiments of the present invention relate to a substantially closed life cycle for catalyst materials. FIG. 3 illustrates one embodiment of such a life cycle 300.

In a first phase of the life cycle 300, some means of nano-particle production provides catalyst nano-particles into a filter system, as illustrated at stage 310. The illustration shows unspecified catalyst nano-particles Ct entrained within an argon stream Ar. The catalyst Ct and argon Ar stream flows into the filter structure, which retains the catalyst nano-particles Ct, while the argon Ar flows through the filter structure. As a result, an activated filter is produced.

Next, at stage 320, the filter structure is isolated. Preferably, a downstream valve is closed, then an upstream valve, and some pressurization of argon Ar is retained within the activated filter structure, along with catalyst nano-particles Ct.

Then, in a second phase of the life cycle, the activated filter structure and catalyst Ct are used as a fixed-bed catalyst for catalyzing a fluid flow, as illustrated at stage 330. In the illustration, a desired gas contaminated with undesired oxygen $O_2$ is provided to the upstream valve. The upstream valve is opened. Gas then flows into the activated filter structure, where catalyst nano-particles Ct catalyze removal of oxygen $O_2$, essentially filtering the oxygen $O_2$ from the mixed gas stream. Downstream, once the downstream valve is opened, the filter structure outputs pure desired gas.

The mechanism by which the catalyst nano-particles Ct remove the oxygen from the gas stream results in oxygen contamination of the catalyst nano-particles Ct. This product, oxidized catalyst nano-particles Ct+O, is reused within the life cycle. Specifically, the oxidized Ct+O nano-particles are combined and/or processed at stage 340 to produce an input to the nano-particle production stage 350. In the illustration, the oxidized Ct+O nano-particles are processed to produce micron scale oxidized catalyst powder Ct+O, which serves as an input to the nano-particle production means at stage 350.

Finally, the nano-particle production means provides an output of catalyst nano-particles to the first phase of the life cycle back at stage 310.

The life cycle of FIG. 3 embodies a method, or methods, of using and reusing catalyst materials in a substantially closed cycle. Although specific gases, catalysts, and catalysis reactions are mentioned with respect to FIG. 3, the present invention is intended to cover variations on these components and configurations of the illustrated life cycle and its related methods.

Figure 4:
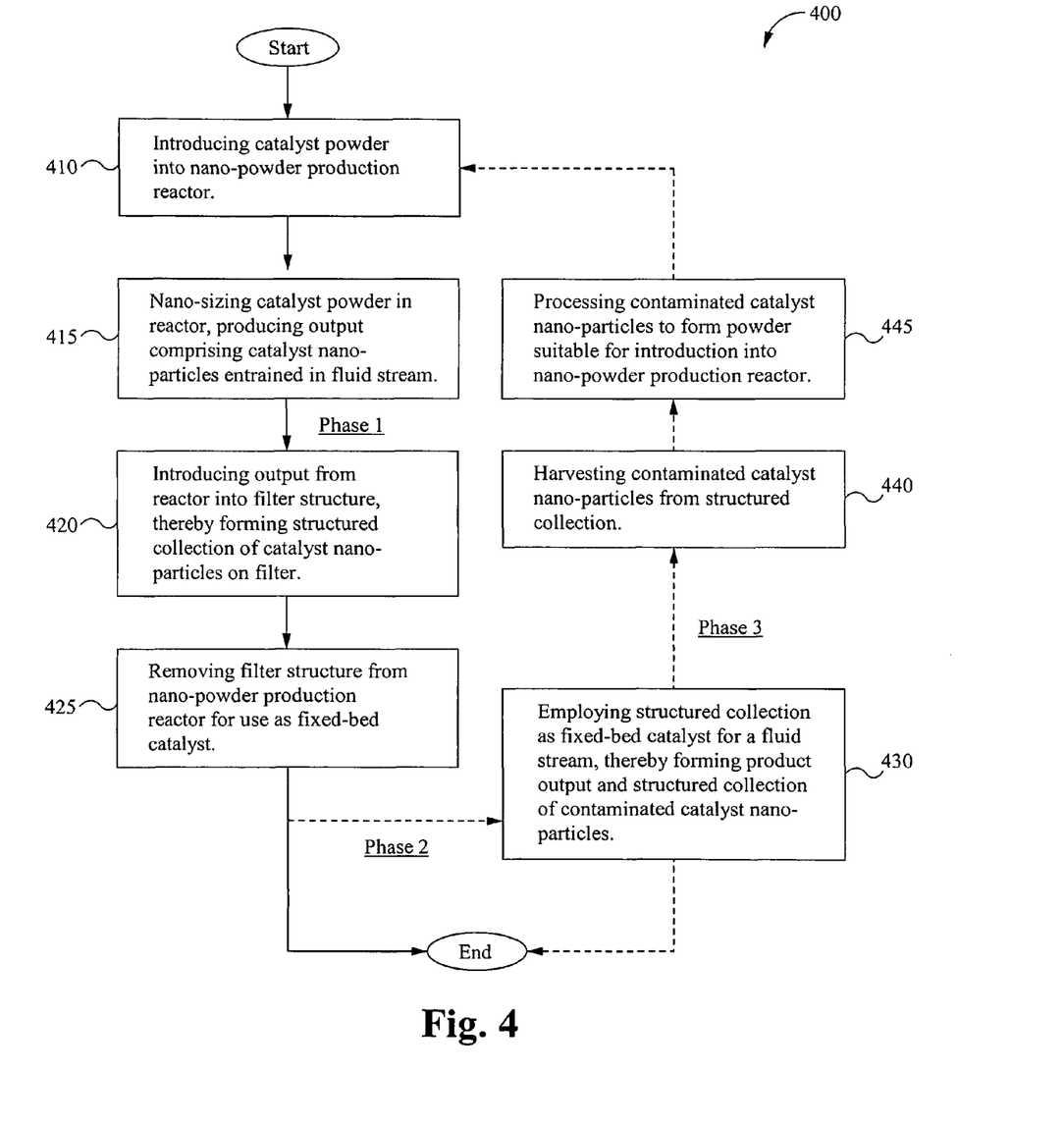
FIG. 4 is a flowchart illustrating one embodiment of a method for producing a fixed bed catalyst, using the fixed bed catalyst, and reusing the catalyst material in accordance with the principles of the present invention.

FIG. 4 is a flow chart illustrating one embodiment of a method 400 for producing a fixed bed catalyst, using the fixed bed catalyst, and reusing the catalyst material in accordance with the principles of the present invention.

At step 410, a starting powder is introduced into the nano-powder production reactor. This starting powder preferably contains catalyst material.

At step 415, the reactor nano-sizes the starting powder, thereby producing a plurality of nano-particles, with each particle containing catalyst material. These nano-particles are preferably entrained in a fluid stream to form an output of the reactor. In a preferred embodiment, the reactor nano-sizes the starting powder by applying a plasma flow to the starting powder, as previously discussed.

At step 420, the output from the reactor is introduced into the filter structure. For example, the output can flow from the reactor into the filter structure. The filter structure filters this fluid stream, separating the catalyst nano-particles from the rest of the fluid stream, and thereby forming a structured collection of catalyst nano-particles on the filter structure.

At step 425, the filter structure can then be removed, or fluidly de-coupled, from the nano-powder production reactor in preparation for its use as a fixed-bed catalyst in a fluid flow. The method 400 may then come to an end.

However, the filter structure can optionally be used as a fixed-bed catalyst for a fluid stream at step 430. In operation as a fixed-bed catalyst, the structured collection of catalyst nano-particles may catalyze the removal of an undesired material from the fluid stream, thereby forming a desired product output, while contaminating the catalyst nano-particles with the undesired material. The method 400 may then come to an end.

However, the collection of contaminated catalyst nano-particles on the filter structure can optionally be harvested at step 440 in preparation for reuse, such as discussed above with respect to the life cycle 300 of FIG. 3.

At step 445, the contaminated catalyst nano-particles are processed to form powder that is suitable for introduction into the nano-powder production reactor. Such processing may include, but is not limited to, combining the nano-particles to form micron-sized powder, with the micron powder containing the catalyst material.

The method may then repeat back at step 410, where the processed catalyst powder can be re-introduced into the nano-powder production reactor.

The embodiments of the present invention provide a variety of systems, methods, and life cycles to permit use and reuse of a catalytic material in nano-particle or nano-powder phase. Preferably, an activated filter including a structured collection of catalyst nano-particles has an effective BET surface area of at least 10,000 times the surface area of a micron scale structure of the same volume. This increase in surface area results in massive cost savings.

Additionally, by using a filter structure to form a structured collection of catalytic nano-particles, the present invention can make the production and use of the catalytic structure significantly more efficient and can enable the reuse of catalytic materials.

The present invention has been described in terms of specific embodiments incorporating details to facilitate the understanding of the principles of construction and operation of the invention. As such, references herein to specific embodiments and details thereof are not intended to limit the scope of the claims appended hereto. It will be apparent to those skilled in the art that modifications can be made to the embodiments chosen for illustration without departing from the spirit and scope of the invention.

What is claimed is:

1. A method of producing a fixed-bed catalyst with nano-scale structure using a nano-powder production reactor and a filter structure, the method comprising:

introducing a starting powder into the nano-powder production reactor, wherein the starting powder comprises catalyst material;

the nano-powder production reactor nano-sizing the starting powder, thereby producing an output, wherein the output comprises a nano-powder entrained in a reactor fluid stream, the nano-powder comprising a plurality of nano-particles, each nano-particle comprising the catalyst material;

introducing the output from the nano-powder production reactor to the filter structure, wherein the filter structure is fluidly coupled to the nano-powder production reactor;

the filter structure separating the nano-particles from the reactor fluid stream, wherein the filter structure collects the nano-particles, thereby forming a structured collection of catalytic nano-particles on the filter structure;

removing the filter structure from the nano-powder production reactor, wherein the structured collection of catalytic nano-particles is maintained on the filter structure for use as a fixed-bed catalyst;

forming a structured collection of contaminated catalytic nano-particles on the filter structure and a product output;

harvesting the contaminated catalytic nano-particles from the filter structure;

processing the contaminated catalytic nano-particles to form recycled starting powder from the contaminated catalytic nano-particles, wherein the recycled starting powder comprises the catalyst material;

introducing the recycled starting powder into the nano-powder production reactor; and     the nano-powder production reactor nano-sizing the recycled starting powder, thereby producing an output, wherein the output comprises a nano-powder entrained in a fluid stream, the nano-powder comprising a plurality of nano-particles, each nano-particle comprising the catalyst material.

2. The method of claim 1, wherein the step of nano-sizing the starting powder includes:

generating a plasma flow within the nano-powder production reactor; and     applying the plasma flow to the starting powder.

3. The method of claim 1, wherein the starting powder has an average grain size greater than or equal to 1 micron.

4. The method of claim 1, wherein the catalyst material is a metal of the transition group VIII of the periodic table of elements.

5. The method of claim 4, wherein the metal is nickel.

6. The method of claim 4, wherein the metal is iron.

7. The method of claim 4, wherein the metal is cobalt.

8. The method of claim 1, wherein:
the reactor fluid stream of the output from the nano-powder production reactor comprises the nano-powder entrained in argon; and
the filter structure separates the catalytic nano-particles from the argon.

9. The method of claim 1, wherein forming a structured collection of contaminated catalytic nano-particles on the filter structure and the product output comprises employing the structured collection of catalytic nano-particles on the filter structure as a fixed-bed catalyst for a catalysis fluid stream.

10. The method of claim 9, wherein the catalysis fluid stream comprises a desired material and an undesired material, and wherein the step of employing the structured collection as a fixed-bed catalyst comprises:
flowing the catalysis fluid stream through the structured collection of contaminated catalytic nano-particles on the filter structure; and
the structured collection of catalytic nano-particles on the filter structure catalyzing the removal of the undesired material from the catalysis fluid stream, wherein the structured collection is contaminated with the undesired material and product output comprises the desired material.

11. The method of claim 10, wherein:
the undesired material in the catalysis fluid stream is oxygen; and
the structured collection of catalytic nano-particles filters the oxygen from the catalysis fluid stream, thereby contaminating the catalytic nano-particles on the filter structure with oxygen.

12. The method of claim 1, wherein the recycled starting powder has an average grain size greater than or equal to 1 micron.

13. A method of producing and using a fixed-bed catalyst with nano-scale structure using a nano-powder production reactor and a filter structure, the method comprising:
introducing a starting powder into the nano powder production reactor, wherein the starting powder comprises catalyst material;
the nano-powder production reactor nano-sizing the starting powder, thereby producing an output, wherein the output comprises a nano-powder entrained in a reactor fluid stream, the nano-powder comprising a plurality of nano-particles, each nano-particle comprising the catalyst material;
introducing the output from the nano-powder production reactor to the filter structure, wherein the filter structure is fluidly coupled to the nano-powder production reactor;
the filter structure separating the nano-particles from the reactor fluid stream, wherein the filter structure collects the nano-particles, thereby forming a structured collection of catalytic nano-particles on the filter structure;
removing the filter structure from the nano-powder production reactor, wherein the structured collection of catalytic nano-particles is maintained on the filter structure for use as a fixed-bed catalyst;
employing the structured collection of catalytic nano-particles on the filter structure as a fixed-bed catalyst for a catalysis fluid stream, thereby forming a structured collection of contaminated catalytic nano-particles on the filter structure and a product output;
harvesting the contaminated catalytic nano-particles from the filter structure;
processing the contaminated catalytic nano-particles to form recycled starting powder from the contaminated catalytic nano-particles, wherein the recycled starting powder comprises the catalyst material;
introducing the recycled starting powder into the nano-powder production reactor; and
the nano-powder production reactor nano-sizing the recycled starting powder, thereby producing an output, wherein the output comprises a nano-powder entrained in a fluid stream, the nano-powder comprising a plurality of nano-particles, each nano-particle comprising the catalyst material.

14. The method of claim 13, wherein:
the step of nano-sizing the starting powder includes:
generating a plasma flow within the nano-powder production reactor, and
applying the plasma flow to the starting powder; and
the step of nano-sizing the recycled starting powder includes:
generating a plasma flow within the nano-powder production reactor, and
applying the plasma flow to the recycled starting powder.

15. The method of claim 13, wherein the starting powder and the recycled starting powder have an average grain size greater than or equal to 1 micron.

16. The method of claim 13, wherein the catalyst material is a metal of the transition group VIII of the periodic table of elements.

17. The method of claim 16, wherein the metal is nickel.
18. The method of claim 16, wherein the metal is iron.
19. The method of claim 16, wherein the metal is cobalt.
20. The method of claim 13, wherein:
the reactor fluid stream of the output from the nano-powder production reactor comprises the nano-powder entrained in argon; and
the filter structure separates the catalytic nano-particles from the argon.

21. The method of claim 13, wherein the catalysis fluid stream comprises a desired material and an undesired material, and wherein the step of employing the structured collection as a fixed-bed catalyst comprises:
flowing the catalysis fluid stream through the structured collection of contaminated catalytic nano-particles on the filter structure; and
the structured collection of catalytic nano-particles on the filter structure catalyzing the removal of the undesired material from the catalysis fluid stream, wherein the structured collection is contaminated with the undesired material and product output comprises the desired material.

22. The method of claim 21, wherein:
the undesired material in the catalysis fluid stream is oxygen; and
the structured collection of catalytic nano-particles filters the oxygen from the catalysis fluid stream, thereby contaminating the catalytic nano-particles on the filter structure with oxygen.

* * * * *